United States Patent
Mihalca et al.

(10) Patent No.: US 11,045,070 B2
(45) Date of Patent: Jun. 29, 2021

(54) ENDOCOUPLER WITH INDUCTION COUPLING

(71) Applicant: Smith & Nephew, Inc., Memphis, TN (US)

(72) Inventors: Gheorghe Mihalca, North Chelmsford, MA (US); Baoduy Tran, Wilmington, MA (US); David Sonnenshein, Somerville, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 0 days.

(21) Appl. No.: 16/751,718

(22) Filed: Jan. 24, 2020

(65) Prior Publication Data

US 2020/0154979 A1    May 21, 2020

Related U.S. Application Data

(63) Continuation of application No. 15/522,215, filed as application No. PCT/US2015/060993 on Nov. 17, 2015, now Pat. No. 10,582,833.

(60) Provisional application No. 62/081,158, filed on Nov. 18, 2014.

(51) Int. Cl.
 *A61B 1/00* (2006.01)
 *A61B 1/04* (2006.01)
 *A61B 1/06* (2006.01)

(52) U.S. Cl.
 CPC ...... *A61B 1/00016* (2013.01); *A61B 1/00029* (2013.01); *A61B 1/00126* (2013.01); *A61B 1/0684* (2013.01); *A61B 1/04* (2013.01); *A61B 1/042* (2013.01)

(58) Field of Classification Search
 CPC combination set(s) only.
 See application file for complete search history.

(56) References Cited

U.S. PATENT DOCUMENTS

| | | |
|---|---|---|
| 5,916,215 A | 6/1999 | Long |
| 6,217,512 B1 | 4/2001 | Salo |
| 7,397,364 B2 * | 7/2008 | Govari ...... A61B 5/06 340/13.27 |

(Continued)

FOREIGN PATENT DOCUMENTS

| | | |
|---|---|---|
| CN | 201323473 Y | 10/2009 |
| EP | 0989384 A2 | 3/2000 |

(Continued)

OTHER PUBLICATIONS

Japanese Application No. 2017-544859—Notice of Reasons for Rejection dated Jan. 28, 2020.

(Continued)

*Primary Examiner* — John P Leubecker
*Assistant Examiner* — Shankar Raj Ghimire

(57) ABSTRACT

Endoscopic systems and methods that provide wireless power transmission from a camera head to at least one solid-state light source housed in an endoscopic device. The endoscopic systems and methods employ a multi-stage electromagnetic induction coupling mechanism that can wirelessly transfer power from the camera head to an endocoupler, as well as from the endocoupler to the solid-state light source, while allowing axial rotational motion of at least the camera head, the endocoupler, and/or the endoscopic device relative to one another.

8 Claims, 8 Drawing Sheets

(56) References Cited

U.S. PATENT DOCUMENTS

| | | | | |
|---|---|---|---|---|
| 7,582,056 B2* | 9/2009 | Noguchi | | A61B 1/015 600/109 |
| 9,646,763 B2* | 5/2017 | Robertson | | H02J 50/10 |
| 9,715,727 B2* | 7/2017 | Mihalca | | H04N 1/6008 |
| 2006/0116550 A1* | 6/2006 | Noguchi | | A61B 1/00121 600/132 |
| 2006/0171693 A1 | 8/2006 | Todd et al. | | |
| 2007/0059989 A1 | 3/2007 | Kura et al. | | |
| 2008/0108865 A1 | 5/2008 | Tamura et al. | | |
| 2009/0171448 A1 | 7/2009 | Eli | | |
| 2010/0141744 A1* | 6/2010 | Amling | | A61B 1/00029 348/68 |
| 2010/0179384 A1 | 7/2010 | Hoeg et al. | | |
| 2011/0018988 A1* | 1/2011 | Kazakevich | | A61B 1/042 348/68 |
| 2011/0025132 A1* | 2/2011 | Sato | | H01Q 7/00 307/104 |
| 2011/0115891 A1* | 5/2011 | Trusty | | A61B 1/00158 348/65 |
| 2011/0193948 A1 | 8/2011 | Amling et al. | | |
| 2014/0021795 A1* | 1/2014 | Robertson | | H02J 50/40 307/104 |
| 2014/0184771 A1* | 7/2014 | Mazzetti | | H02J 5/00 348/75 |
| 2015/0062153 A1* | 3/2015 | Mihalca | | A61B 1/00135 345/604 |
| 2015/0366434 A1* | 12/2015 | Tsuruta | | A61B 1/00071 600/104 |
| 2015/0366441 A1 | 12/2015 | Tsuruta et al. | | |
| 2016/0128550 A1 | 5/2016 | Laser et al. | | |
| 2017/0035402 A1* | 2/2017 | Matsui | | H02J 50/12 |
| 2017/0332881 A1* | 11/2017 | Matsuki | | A61B 1/00029 |

FOREIGN PATENT DOCUMENTS

| | | |
|---|---|---|
| EP | 2422687 A1 | 2/2012 |
| WO | 2008063565 A2 | 5/2008 |

OTHER PUBLICATIONS

Chinese Application No. 201580062821.0 Decision on Rejection & Text of Decision of Rejection dated Dec. 30, 2019.

Indian Office Action for Application No. 201717015333 dated Feb. 27, 2020, 7 pages.

Chinese office dated Mar. 28, 2019 in corresponding Chinese application 201580062821.0; 8 pages.

Japanese office action dated May 13, 2019 in corresponding Japanese application 2017-544859; 3 pages.

MX Office Action for Application No. MX/a/2017/006482 dated Nov. 24, 2020, 3 pages.

* cited by examiner

ENDOCOUPLER WITH INDUCTION COUPLING

CROSS REFERENCE TO RELATED APPLICATIONS

This application is a continuation of U.S. application Ser. No. 15/522,215 filed Apr. 26, 2017 titled "ENDOCOUPLER WITH INDUCTION COUPLING." The Ser. No. 15/522,215 application was a National phase entry of PCT/US2015/060993 filed Nov. 17, 2015. The PCT/US2015/060993 application claims benefit of the priority of U.S. Provisional Patent Application No. 62/081,158 filed Nov. 18, 2014 titled "ENDOCOUPLER WITH INDUCTION COUPLING." All the noted applications are incorporated by reference herein as if reproduced in full below.

TECHNICAL FIELD

The present application relates generally to endoscopic systems and methods, and more specifically to systems and methods of providing wireless power transmission from a camera head to one or more solid-state light sources housed in an endoscopic device.

BACKGROUND

Surgeons and other medical professionals frequently employ endoscopic systems and methods to inspect regions within a patient's body during surgical, diagnostic, and/or other medical procedures. For example, a surgeon may employ an endoscopic system to inspect a patient's abdominal or pelvic cavity during a laparoscopic procedure, or to inspect a patient's thoracic or chest cavity during a thoracoscopic procedure. Such an endoscopic system may be employed in conjunction with surgical instruments such as forceps, scissors, probes, etc., to perform such a laparoscopic or thoracoscopic procedure through a small incision made in the patient's body, avoiding the need to open the patient's abdomen or chest. In this way, the patient's pain and/or discomfort due to the medical procedure, as well as the patient's recovery time, can be reduced.

A conventional endoscopic system typically includes a camera head, an endocoupler, an endoscopic device, a light source, and a light cable. The endocoupler mechanically and optically couples the camera head to the endoscopic device, and the light cable connects the light source to the endoscopic device. The endoscopic device typically includes an elongated insertion tube that extends from the endocoupler to a distal end of the endoscopic device, as well as an optical fiber bundle that provides an optical path for directing light energy produced by the light source to the distal end of the endoscopic device.

The conventional endoscopic system described above has drawbacks, however, due at least to the low efficiency and high power of the light source. Such a light source is typically a lamp that can require as much as 300 Watts of power or more in order to deliver about 1 Watt of light to the distal end of the endoscopic device, resulting in an efficiency of about 0.3%. Moreover, the light source in combination with the light cable can be bulky and can add needless clutter to the surgical suite, as well as significantly increase the overall cost of the endoscopic system.

It would therefore be desirable to have systems and methods of implementing a light source in an endoscopic system that can avoid at least some of the drawbacks of conventional endoscopic systems.

SUMMARY

In accordance with the present application, endoscopic systems and methods are disclosed that provide wireless power transmission from a camera head to at least one solid-state light source housed in an endoscopic device. The disclosed endoscopic systems and methods employ a multi-stage electromagnetic induction coupling mechanism that can wirelessly transfer power from the camera head to an endocoupler, as well as from the endocoupler to the solid-state light source, while allowing axial rotational motion of at least the camera head, the endocoupler, and/or the endoscopic device relative to one another.

In one aspect, an exemplary endoscopic system includes a camera head, an endoscopic device, and an endocoupler that couples the camera head to the endoscopic device. The camera head is coupled to a proximal region of the endocoupler, and the endoscopic device is coupled to a distal region of the endocoupler. In an exemplary aspect, the endoscopic device can be a direct-view endoscope. The endoscopic device includes an elongated insertion tube, an illumination post housing, and an optical fiber bundle. The elongated insertion tube, which can be rigid or flexible, extends from about the distal region of the endocoupler to a distal end section of the endoscopic device. The illumination post housing can house at least one solid-state light source. In a further exemplary aspect, the solid-state light source can be a light-emitting diode (LED). The optical fiber bundle of the elongated insertion tube provides an optical path for directing light energy produced by the solid-state light source to the distal end section of the endoscopic device.

In this aspect, the endoscopic system further includes a multi-stage electromagnetic induction coupling mechanism that can wirelessly transfer power from the camera head to the endocoupler, as well as from the endocoupler to the solid-state light source housed in the illumination post housing, while allowing axial rotational motion of at least the camera head, the endocoupler, and/or the endoscopic device relative to one another. In an exemplary aspect, the multi-stage electromagnetic induction coupling mechanism includes at least a first rotary induction coupling stage and a second rotary induction coupling stage. The first rotary induction coupling stage is disposed between the camera head and the endocoupler at or near the proximal region of the endocoupler. The second rotary induction coupling stage is disposed between the endocoupler and the endoscopic device at or near the distal region of the endocoupler. In a further exemplary aspect, the first and second rotary induction coupling stages can each include a first coil/ferrite assembly that has a magnetic field generating coil wound around a first ferrite core, and a second coil/ferrite assembly that has a magnetic field capturing coil wound around a second ferrite core. In order to allow axial rotational motion of the camera head and the endocoupler relative to one another, the first and second coil/ferrite assemblies included in the first rotary induction coupling stage can be implemented as a rotary power transfer device, such as a rotary transformer. The first rotary induction coupling stage can further include a first rotary attachment mechanism, such as a threaded mount, for rotatably attaching the endocoupler to the camera head. In order to allow axial rotational motion of the endoscopic device and the endocoupler relative to one another, the first and second coil/ferrite assemblies included in the second rotary induction coupling stage can likewise be implemented as a rotary power transfer device, such as a rotary transformer. The second rotary induction coupling stage can further include a second rotary attachment mechanism, such as a rotary joint, for rotatably attaching the endocoupler to the endoscopic device.

In an exemplary mode of operation, an endoscopic system is provided that includes a camera head, an endoscopic device, an endocoupler coupling the camera head to the endoscopic device, a first rotary induction coupling stage disposed between the camera head and the endocoupler, and a second rotary induction coupling stage disposed between the endocoupler and the endoscopic device, which houses at least one solid-state light source. Power is provided, by the camera head, for powering the solid-state light source by providing a first alternating current (also referred to herein as the "first AC current") to a first coil/ferrite assembly within the first rotary induction coupling stage, thereby causing a first magnetic field to be generated by the first coil/ferrite assembly of the first rotary induction coupling stage. The first magnetic field generated by the first coil/ferrite assembly of the first rotary induction coupling stage is captured by a second coil/ferrite assembly within the first rotary induction coupling stage, thereby causing a second alternating current (also referred to herein as the "second AC current") to be induced in the second coil/ferrite assembly of the first rotary induction coupling stage. The second AC current is provided to a first coil/ferrite assembly within the second rotary induction coupling stage, thereby causing a second magnetic field to be generated by the first coil/ferrite assembly of the second rotary induction coupling stage. The second magnetic field generated by the first coil/ferrite assembly of the second rotary induction coupling stage is captured by a second coil/ferrite assembly within the second rotary induction coupling stage, thereby causing a third alternating current (also referred to herein as the "third AC current") to be induced in the second coil/ferrite assembly of the second rotary induction coupling stage. The third AC current is converted to a direct current (also referred to herein as the "DC current"), which is provided for powering the solid-state light source housed in the illumination post housing of the endoscopic device. Having powered the solid-state light source, the endoscopic device is rotated, by a user, about its axis at the second rotary induction coupling stage in order to change the orientation of a distal end section of the endoscopic device, while maintaining the transfer of power by the second rotary induction coupling stage from the endocoupler to the solid-state light source housed in the endoscopic device. Once having changed the orientation of the distal end section of the endoscopic device, a focusing ring assembly implemented in the endocoupler is rotated, by the user, about its axis at the first rotary induction coupling stage in order to adjust focusing optics contained in the endocoupler and/or the camera head, while further maintaining the transfer of power by the first rotary induction coupling stage from the camera head to the endocoupler, and ultimately to the solid-state light source.

By providing an endoscopic system that includes a camera head, an endoscopic device, an endocoupler coupling the camera head to the endoscopic device, a first rotary induction coupling stage disposed between the camera head and the endocoupler, and at least a second rotary induction coupling stage disposed between the endocoupler and the endoscopic device, a user (e.g., a surgeon or other medical professional) can axially rotate the endoscopic device at the second rotary induction coupling stage relative to the endocoupler, and also axially rotate a focusing ring assembly implemented in the endocoupler at the first rotary induction coupling stage relative to the camera head, while advantageously maintaining a transfer of power from the camera head to the endocoupler across the first rotary induction coupling stage, as well as from the endocoupler to the endoscopic device across the second rotary induction coupling stage, for powering a solid-state light source housed in the endoscopic device. Such a solid-state light source (e.g., an LED) can require about 5 Watts of power in order to deliver about 1 Watt of light to a distal end of the endoscopic device, advantageously resulting in an increased efficiency of about 20%.

Other features, functions, and aspects of the invention will be evident from the Detailed Description that follows.

BRIEF DESCRIPTION OF THE DRAWINGS

The accompanying drawings, which are incorporated in and constitute a part of this specification, illustrate one or more embodiments described herein and, together with the Detailed Description, explain these embodiments. In the drawings.

DETAILED DESCRIPTION

The disclosure of U.S. Provisional Patent Application No. 62/081,158 filed Nov. 18, 2014 entitled ENDOCOUPLER WITH INDUCTION COUPLING is hereby incorporated herein by reference in its entirety.

Endoscopic systems and methods are disclosed that provide wireless power transmission from a camera head to at least one solid-state light source housed in an endoscopic device. The disclosed endoscopic systems and methods employ a multi-stage electromagnetic induction coupling mechanism that can wirelessly transfer power from the camera head to an endocoupler, as well as from the endocoupler to the solid-state light source, while allowing axial rotational motion of at least the camera head, the endocoupler, and/or the endoscopic device relative to one another.

Figure 1:
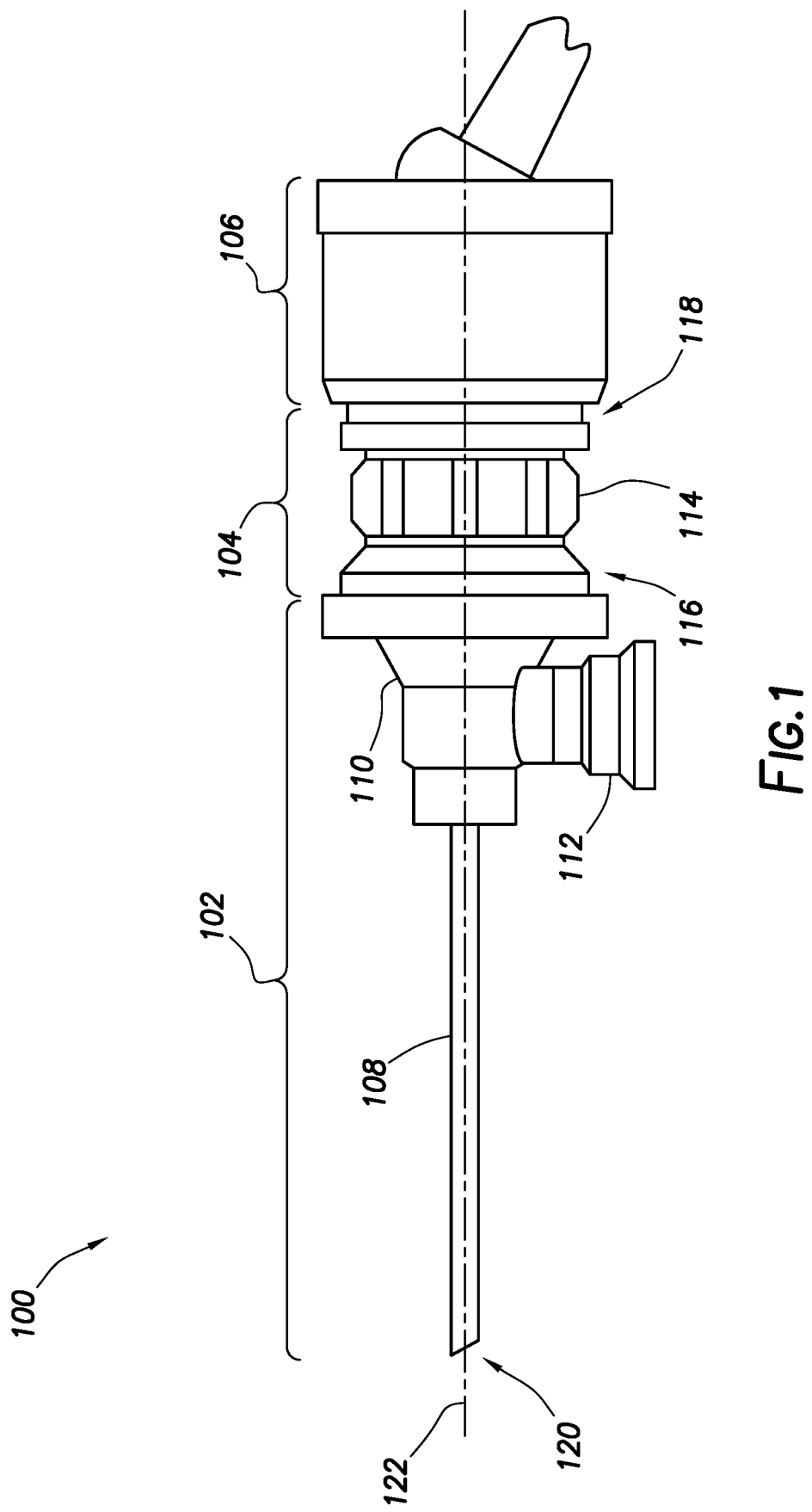
FIG. 1 is a diagram of an exemplary endoscopic system, including a camera head, an endoscopic device, and an endocoupler coupling the camera head to the endoscopic device, in accordance with the present application.

FIG. 1 depicts an illustrative embodiment of an exemplary endoscopic system 100, in accordance with the present application. As shown in FIG. 1, the endoscopic system 100 includes a camera head 106, an endoscopic device 102, and an endocoupler 104 configured to couple the camera head 106 to the endoscopic device 102. For example, a surgeon or other medical professional may employ the endoscopic system 100 to inspect a region within a patient's body during a laparoscopic procedure, a thoracoscopic procedure, or any other suitable surgical, diagnostic, or other medical procedure. The endoscopic device 102 includes an elongated insertion tube 108, an eyepiece section 110, and an illumination post housing 112 for housing at least one solid-state light source (e.g., a solid-state light source 513; see FIG. 5a). The endocoupler 104 includes a focusing ring 114 of a focus assembly (e.g., a focus assembly 514; see FIG. 5a) for adjusting focusing optics (e.g., at least one lens 218; see FIG. 2) contained in the endocoupler 104 and/or the camera head 106. Through the focusing optics, the endocoupler 104 can project an image viewed through the eyepiece section 110 of the endoscopic device 102 onto an imaging sensor of the camera head 106. The camera head 106 is coupled to a proximal region 118 of the endocoupler 104, and the endoscopic device 102 is coupled to a distal region 116 of the endocoupler 104. In one embodiment, the endoscopic device 102 can be a direct-view endoscope, or any other suitable endoscope. The elongated insertion tube 108, which can be rigid or flexible, extends from the eyepiece section 110 to a distal end section 120 of the endoscopic device 102. In one embodiment, the solid-state light source 513 (see FIG. 5a) can be a light-emitting diode (LED). The elongated insertion tube 108 can include an optical fiber bundle (e.g., an optical fiber bundle 521; see FIG. 5a) in order to provide an optical path for directing light energy produced by the solid-state light source to the distal end section 120 of the endoscopic device 102.

Figure 2:
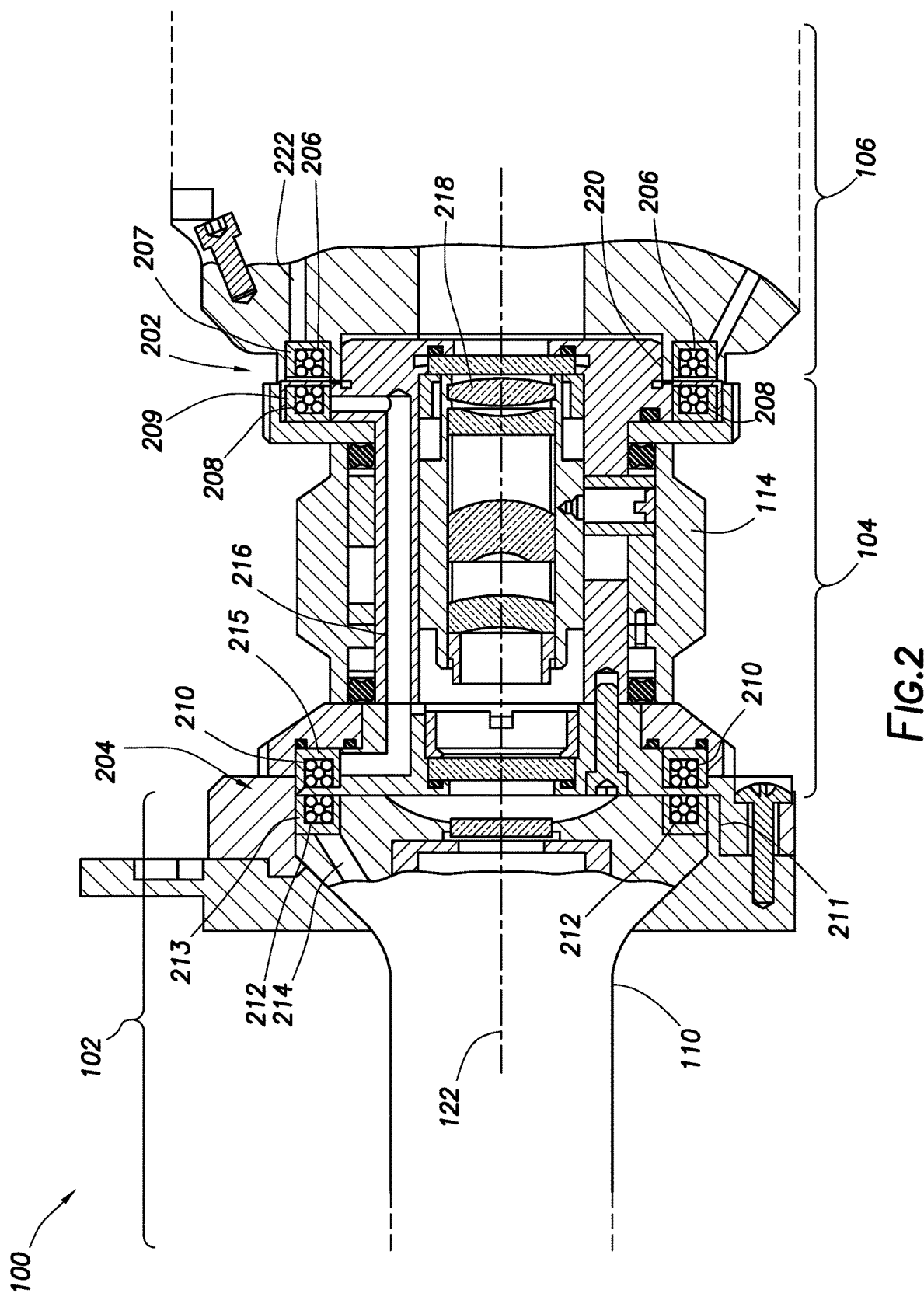
FIG. 2 is a detailed partially cross-sectional view of the camera head, the endocoupler, and the endoscopic device included in the endoscopic system of FIG. 1.

The disclosed endoscopic system 100 further includes a multi-stage electromagnetic induction coupling mechanism that can wirelessly transfer power from the camera head 106 to the endocoupler 104, as well as from the endocoupler 104 to the solid-state light source housed in the illumination post housing 112, while allowing rotational motion, about an axis 122, of at least the camera head 106, the endocoupler 104, and/or the endoscopic device 102 relative to one another. As shown in FIG. 2, the multi-stage electromagnetic induction coupling mechanism can include at least a first rotary induction coupling stage 202 and a second rotary induction coupling stage 204. The first rotary induction coupling stage 202 is disposed between the camera head 106 and the endocoupler 104 at or near the proximal region 118 of the endocoupler 104. The second rotary induction coupling stage 204 is disposed between the endocoupler 104 and the endoscopic device 102 at or near the distal region 116 of the endocoupler 104.

As further shown in FIG. 2, the first rotary induction coupling stage 202 can include a first coil/ferrite assembly (not numbered) that has a magnetic field generating coil 206 wound around a ferrite core 207, and a second coil/ferrite assembly (not numbered) that has a magnetic field capturing coil 208 wound around a ferrite core 209. The first coil/ferrite assembly and the second coil/ferrite assembly of the first rotary induction coupling stage 202 are disposed longitudinally about the axis 122 of the endoscopic system 100. In order to allow axial rotational motion of the camera head 106 and the endocoupler 104 relative to one another, the first and second coil/ferrite assemblies of the first rotary induction coupling stage 202 can be implemented as a rotary transformer or any other suitable rotary power transfer device. In the case where the first and second coil/ferrite assemblies of the first rotary induction coupling stage 202 are implemented as a rotary transformer, one of the coil/ferrite assemblies can have a fixed coil, while the other coil/ferrite assembly has a rotatable coil. The first rotary induction coupling stage 202 can further include a threaded mount 220, such as a C-mount or any other suitable rotary attachment mechanism, for use in rotatably attaching the endocoupler 104 to the camera head 106.

With regard to FIG. 2, the second rotary induction coupling stage 204 of the endoscopic system 100 can include a first coil/ferrite assembly (not numbered) that has a magnetic field generating coil 210 wound around a ferrite core 215, and a second coil/ferrite assembly (not numbered) that has a magnetic field capturing coil 212 wound around a ferrite core 213. The first coil/ferrite assembly and the second coil/ferrite assembly of the second rotary induction coupling stage 204 are disposed longitudinally about the axis 122 of the endoscopic system 100. In order to allow axial rotational motion of the endoscopic device 102 and the endocoupler 104 relative to one another, the first and second coil/ferrite assemblies of the second rotary induction coupling stage 204 can be implemented as a rotary transformer or any other suitable rotary power transfer device. In the case where the first and second coil/ferrite assemblies of the second rotary induction coupling stage 204 are implemented as a rotary transformer, one of the coil/ferrite assemblies can have a fixed coil, while the other coil/ferrite assembly has a rotatable coil. The second rotary induction coupling stage 204 can further include a rotary joint 211 or any other suitable rotary attachment mechanism, for use in rotatably attaching the endocoupler 104 to the endoscopic device 102.

In one mode of operation, an alternating current (AC) source (also referred to herein as the "AC current source") (e.g., an AC current source 616; see FIG. 6) provides, via a first conductor disposed in a channel 222, a first AC current to the first coil/ferrite assembly of the first rotary induction coupling stage 202, causing a first magnetic field to be generated by the magnetic field generating coil 206. The magnetic field capturing coil 208 included in the second coil/ferrite assembly of the first rotary induction coupling stage 202 captures the first magnetic field generated by the magnetic field generating coil 206, causing a second AC current to be induced in the magnetic field capturing coil 208. A second conductor disposed in a channel 216 provides the second AC current to the first coil/ferrite assembly of the second rotary induction coupling stage 204, causing a second magnetic field to be generated by the magnetic field generating coil 210. The magnetic field capturing coil 212 included in the second coil/ferrite assembly of the second rotary induction coupling stage 204 captures the second magnetic field generated by the magnetic field generating coil 210, causing a third AC current to be induced in the magnetic field capturing coil 212. A third conductor disposed in a channel 214 provides the third AC current to a rectifier circuit (e.g., a rectifier circuit 523; see FIG. 5a), such as a bridge rectifier or any other suitable rectifier circuit, which converts the third AC current to a direct current (also referred to herein as the "DC current") for powering the solid-state light source (e.g., an LED) housed in the illumination post housing 112 of the endoscopic device 102. Having powered the solid-state light source of the endoscopic device 102, the endoscopic device 102 can be rotated, by a user (e.g., a surgeon or other medical professional), about the axis 122 at the second rotary induction coupling stage 204 in order to change the orientation of the distal end section 120 of the endoscopic device 102, while maintaining the transfer of power by the first and second coil/ferrite assemblies (e.g., a rotary transformer) of the second rotary induction coupling stage 204 from the endocoupler 104 to the solid-state light source. Once having changed the orientation of the distal end section 120 of the endoscopic device 102, the focusing ring 114 of the focus assembly can be rotated, by the user, about the axis 122 at the first rotary induction coupling stage 202 in order to adjust the focusing optics contained in the endocoupler 104 and/or the camera head 106, while further maintaining the transfer of power by the first and second coil/ferrite assemblies (e.g., another rotary transformer) of the first rotary induction coupling stage 202 from the camera head 106 to the endocoupler 104.

Figure 3:
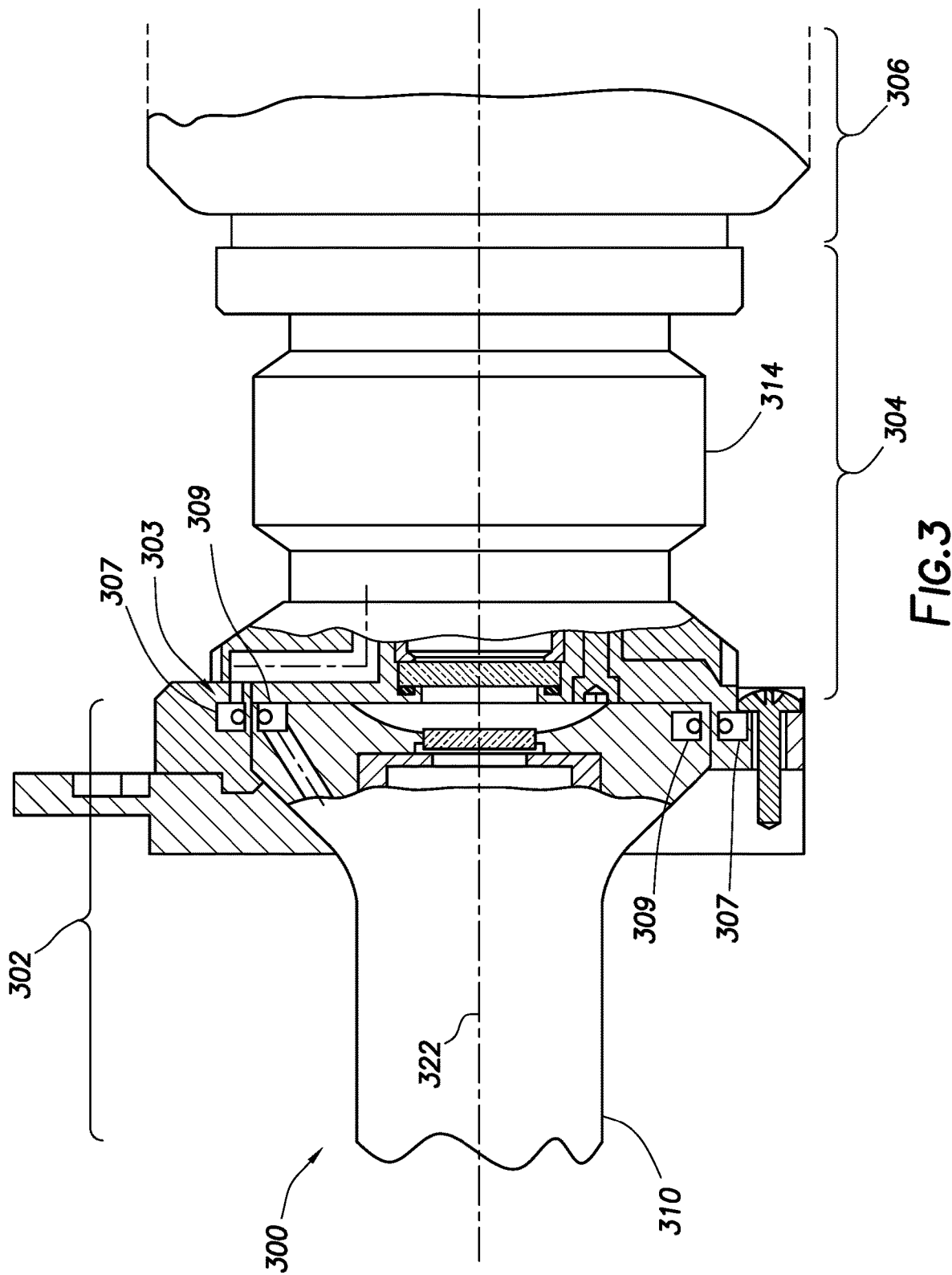
FIG. 3 is a detailed partially cross-sectional view of an endocoupler and an endoscopic device included in a first alternative embodiment of the endoscopic system of FIG. 1.

FIG. 3 depicts a first alternative embodiment of the endoscopic system 100 of FIG. 1. As shown in FIG. 3, an endoscopic system 300 includes a camera head 306, an endoscopic device 302, and an endocoupler 304 configured to couple the camera head 306 to the endoscopic device 302. The endoscopic device 302 includes an eyepiece section 310. The endocoupler 104 includes a focusing ring 314 of a focus assembly for adjusting focusing optics contained in the endocoupler 304 and/or the camera head 306. The endoscopic system 300 further includes a multi-stage electromagnetic induction coupling mechanism that can wirelessly transfer power from the camera head 306 to the endocoupler 304, as well as from the endocoupler 304 to a solid-state light source (e.g., an LED) housed in the endoscopic device 302, while allowing rotational motion, about an axis 322, of at least the camera head 306, the endocoupler 304, and/or the endoscopic device 302 relative to one another. As further shown in FIG. 3, the multi-stage electromagnetic induction coupling mechanism can include at least a rotary induction coupling stage 303 disposed between the endocoupler 304 and the endoscopic device 302 at or near a distal region of the endocoupler 304. The rotary induction coupling stage 303 can include a first coil/ferrite assembly 307 and a second coil/ferrite assembly 309. Another such rotary induction coupling stage, which can be disposed between the camera head 306 and the endocoupler 304 at or near a proximal region of the endocoupler 304, is not shown for clarity of illustration. Whereas the first and second coil/ferrite assemblies of the rotary induction coupling stage 204 (see FIG. 2) (as well as the first and second coil/ferrite assemblies of the rotary induction coupling stage 202; see also FIG. 2) are disposed longitudinally about the axis 122 of the endoscopic system 100, the first and second coil/ferrite assemblies 307, 309 of the rotary induction coupling stage 303 (see FIG. 3) are disposed radially about the axis 322 of the endoscopic system 300. In one embodiment, the radially disposed first and second coil/ferrite assemblies 307, 309 can each include a single-turn coil, which can be implemented using a single enameled wire, a plurality of litz wires, or any other suitable wire(s).

Figure 4:
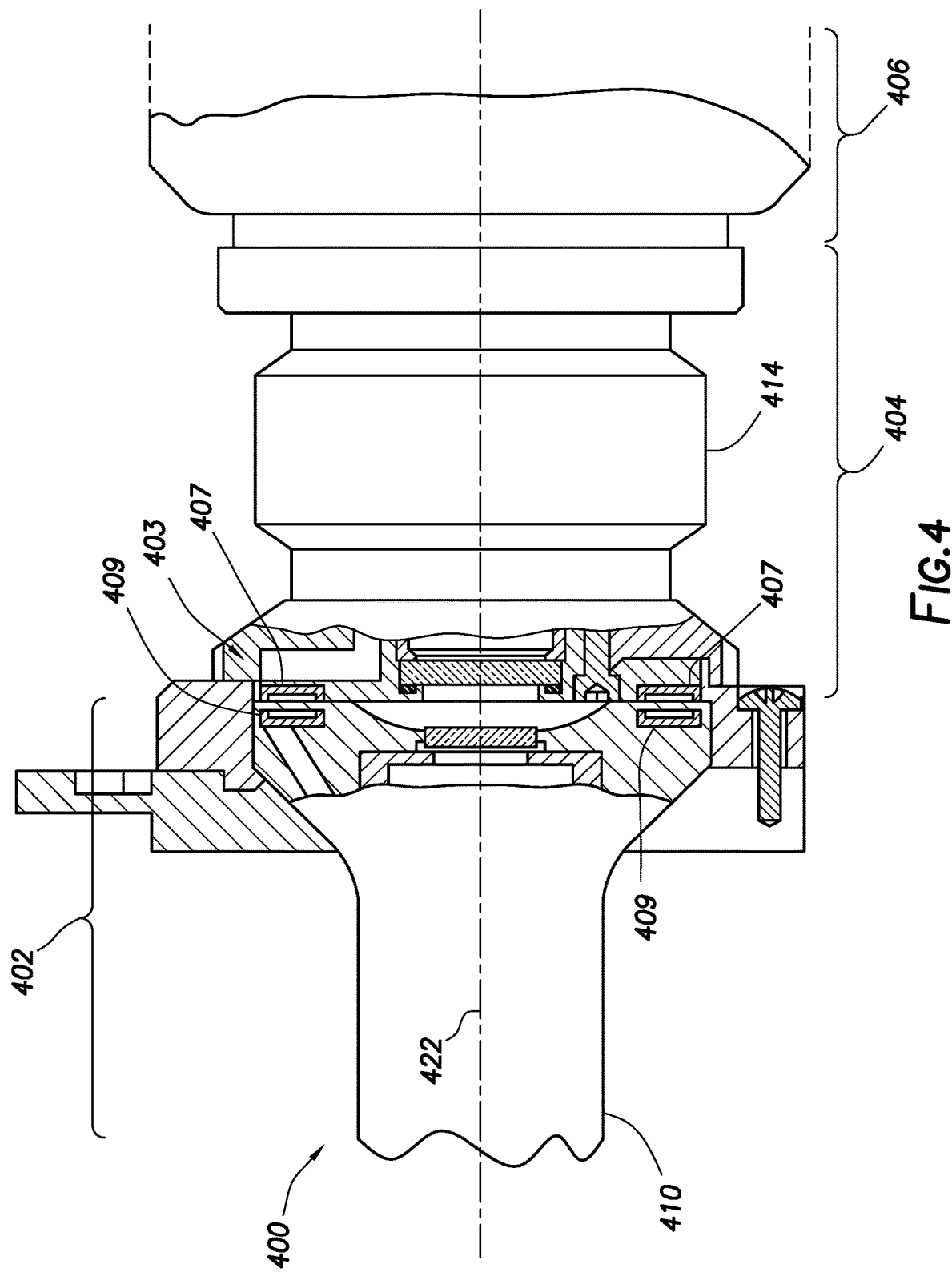
FIG. 4 is a detailed partially cross-sectional view of an endocoupler and an endoscopic device included in a second alternative embodiment of the endoscopic system of FIG. 1.

FIG. 4 depicts a second alternative embodiment of the endoscopic system 100 of FIG. 1. As shown in FIG. 4, an endoscopic system 400 includes a camera head 406, an endoscopic device 402, and an endocoupler 404 configured to couple the camera head 406 to the endoscopic device 402. The endoscopic device 402 includes an eyepiece section 410. The endocoupler 404 includes a focusing ring 414 of a focus assembly for adjusting focusing optics contained in the endocoupler 404 and/or the camera head 406. The endoscopic system 400 further includes a multi-stage electromagnetic induction coupling mechanism that can wirelessly transfer power from the camera head 406 to the endocoupler 404, as well as from the endocoupler 404 to a solid-state light source (e.g., an LED) housed in the endoscopic device 402, while allowing rotational motion, about an axis 422, of at least the camera head 406, the endocoupler 404, and/or the endoscopic device 402 relative to one another. As further shown in FIG. 4, the multi-stage electromagnetic induction coupling mechanism can include at least a rotary induction coupling stage 403 disposed between the endocoupler 404 and the endoscopic device 402 at or near a distal region of the endocoupler 404. The rotary induction coupling stage 403 can include a first coil/ferrite assembly 407 and a second coil/ferrite assembly 409. Another such rotary induction coupling stage, which can be disposed between the camera head 406 and the endocoupler 404 at or near a proximal region of the endocoupler 404, is not shown for clarity of illustration. Whereas the first and second coil/ferrite assemblies 307, 309 of the endoscopic system 300 can each include a single-turn coil (e.g., a single enameled wire, a plurality of litz wires), which typically has a round cross-section, the first and second coil/ferrite assemblies 407, 409 of the endoscopic system 400 can each include a coil that has a non-round cross-section, such as a flat cross-section. In one embodiment, the first and second coil/ferrite assemblies 407, 409 can each include a coil implemented using a flat or ribbon wire, or any other suitable wide thin conductor. By implementing the coils of the first and second coil/ferrite assemblies 407, 409 using wide thin conductors, improved coupling between the coils (and therefore improved power transmission efficiency) can be achieved due to the skin effect, i.e., the distribution of AC current that can occur at the surfaces of such wide thin conductors.

Figure 5A:
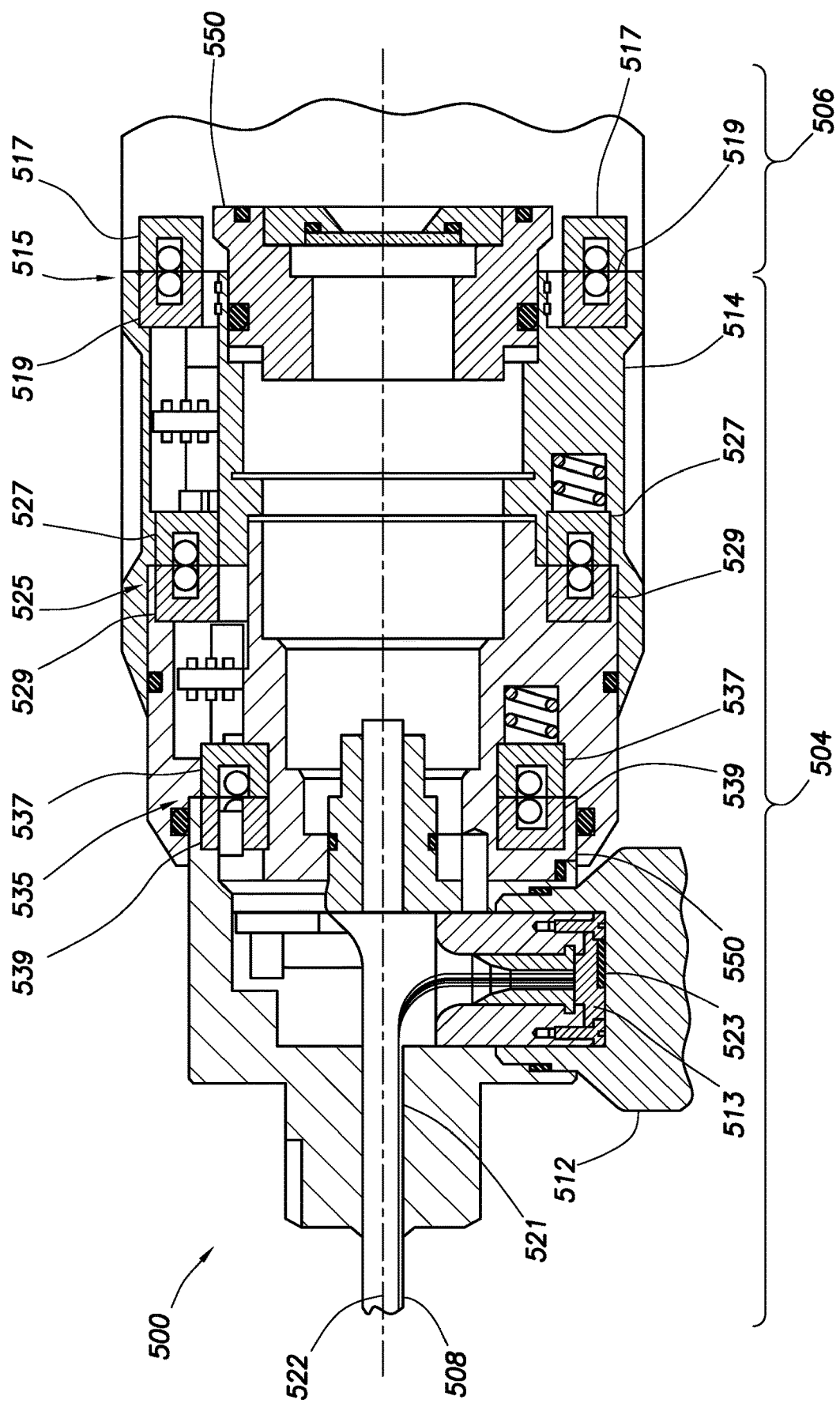
FIG. 5a is a detailed cross-sectional view of a camera head and a video endoscopic device included in a video endoscopic system, in accordance with the present application.

FIG. 5a depicts an illustrative embodiment of an exemplary video endoscopic system 500, in accordance with the present application. As shown in FIG. 5a, the video endoscopic system 500 includes a camera head 506, and a combined video endoscope/endocoupler device 504 coupled to the camera head 506. The video endoscope/endocoupler device 504 includes an elongated insertion tube 508, and an illumination post housing 512 for housing the solid-state light source 513 (e.g., an LED). The video endoscope/endocoupler device 504 further includes the focus assembly 514 adjacent a proximal region of the video endoscope/endocoupler device 504 for adjusting focusing optics contained in the video endoscope/endocoupler device 504 and/or the camera head 506. The camera head 506 is coupleable to the proximal region of the video endoscope/endocoupler device 504. The elongated insertion tube 508, which can be rigid or flexible, extends from a distal region of the video endoscope/endocoupler device 504 to a distal end section of the video endoscopic system 500. The elongated insertion tube 508 includes the optical fiber bundle 521 for use in providing an optical path for directing light energy produced by the solid-state light source 513 to the distal end section of the video endoscopic system 500.

With regard to FIG. 5a, the video endoscopic system 500 further includes a multi-stage electromagnetic induction coupling mechanism that can wirelessly transfer power from the camera head 506 to the video endoscope/endocoupler device 504, and ultimately to the solid-state light source 513 housed in the illumination post housing 512, while allowing rotational motion, about an axis 522, of at least the camera head 506 and the video endoscope/endocoupler device 504 (including the focus assembly 514) relative to one another. As shown in FIG. 5a, the multi-stage electromagnetic induction coupling mechanism can include at least three stages, namely, a first rotary induction coupling stage 515, a second rotary induction coupling stage 525, and a third rotary induction coupling stage 535. For example, the first, second, and third rotary induction coupling stages 515, 525, 535 can each be implemented as a rotary transformer or any other suitable rotary power transfer device. The first rotary induction coupling stage 515 is disposed between the camera head 506 and the video endoscope/endocoupler device 504 at or near the proximal region of the video endoscope/endocoupler device 504. The focus assembly 514 is disposed between the first rotary induction coupling stage 515 and the second rotary induction coupling stage 525. The second rotary induction coupling stage 525 is disposed between the focus assembly 514 and the third rotary induction coupling stage 535. The third rotary induction coupling stage 535 is disposed at or near the distal region of the video endoscope/endocoupler device 504.

With further regard to FIG. 5a, the first rotary induction coupling stage 515 can include a first coil/ferrite assembly 517 and a second coil/ferrite assembly 519. The first and second coil/ferrite assemblies 517, 519 can be disposed longitudinally (or radially) about the axis 522 of the video endoscopic system 500. In order to allow axial rotational motion of the camera head 506 and the video endoscope/endocoupler device 504 relative to one another, the first rotary induction coupling stage 515 can include a threaded mount 550, such as a C-mount or any other suitable rotary attachment mechanism, for use in rotatably attaching the video endoscope/endocoupler device 504 to the camera head 506. The second rotary induction coupling stage 525 can include a first coil/ferrite assembly 527 and a second coil/ferrite assembly 529. The first and second coil/ferrite assemblies 527, 529 can be disposed longitudinally (or radially) about the axis 522 of the video endoscopic system 500. The first and second rotary induction coupling stages 515, 525 are configured to allow rotational motion of the focus assembly 514 disposed therebetween about the axis 522 of the video endoscopic system 500. The third rotary induction coupling stage 535 can include a first coil/ferrite assembly 537 and a second coil/ferrite assembly 539. The first and second coil/ferrite assemblies 537, 539 can be disposed longitudinally (or radially) about the axis 522 of the video endoscopic system 500. In order to allow axial rotational motion of the distal region of the video endoscope/endocoupler device 504 for changing the orientation of the distal end section of the video endoscopic system 500, the third rotary induction coupling stage 535 can include a rotary joint 550 or any other suitable mechanism configured to allow such axial rotational motion.

Figure 5C:
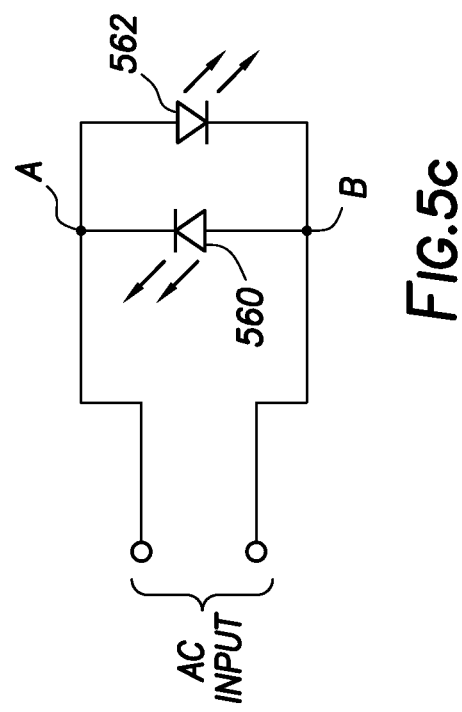
FIG. 5c is a schematic diagram of an alternative embodiment of the circuit of FIG. 5b, in which two solid-state light sources connected in anti-parallel fashion are powered by the AC input.
Figure 5B:
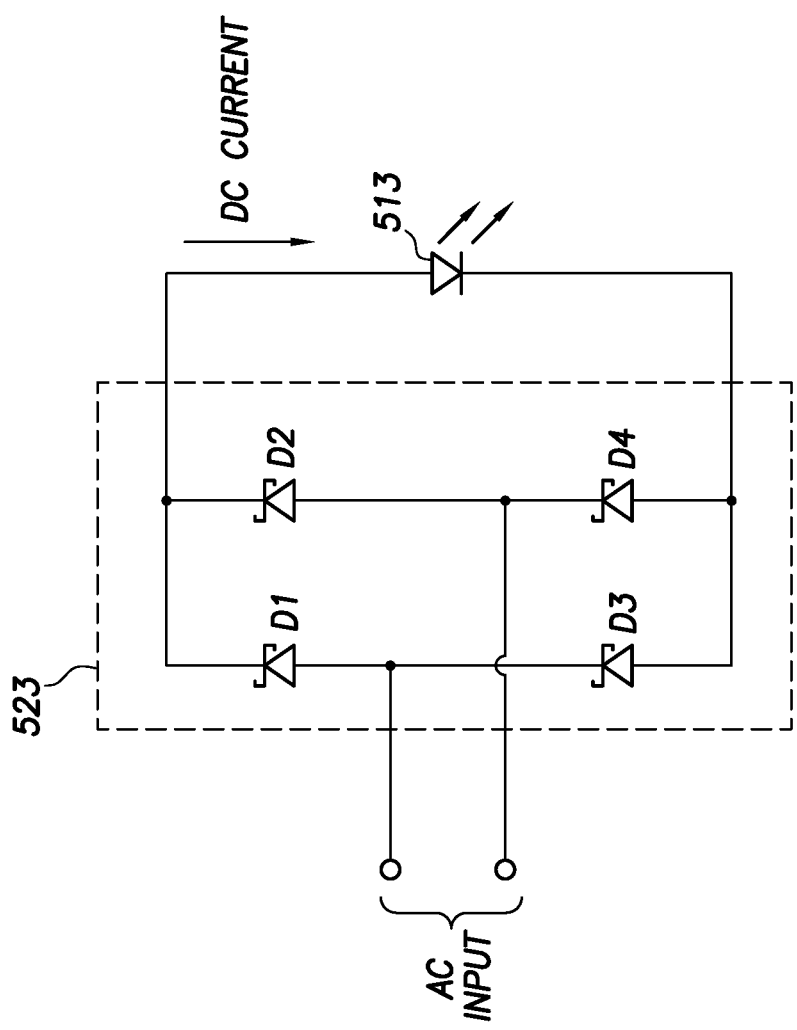
FIG. 5b is a schematic diagram of an exemplary rectifier circuit and an exemplary solid-state light source included in the video endoscopic system of FIG. 5a, the rectifier circuit being configured to convert an alternating current (AC) input to a direct current (DC) for powering the solid-state light source.

As shown in FIG. 5a, the video endoscopic system 500 includes the rectifier circuit 523 that can convert an AC current provided by the third rotary induction coupling stage 535 to a DC current for powering the solid-state light source 513 (e.g., an LED) housed in the illumination post housing 512. FIG. 5b depicts an illustrative embodiment of the rectifier circuit 523, which includes a plurality of diodes D1, D2, D3, D4 configured as a bridge rectifier operative to receive the AC current as input, and to convert the AC input to a DC current for powering the LED 513. FIG. 5c depicts an alternative embodiment of the circuit of FIG. 5b, in which the LED 513 is replaced by a plurality of solid-state light sources 560, 562 (e.g., at least two LEDs) connected in anti-parallel fashion. The plurality of LEDs 560, 562 are powered directly by the AC input, obviating the need for the rectifier circuit 523. As shown in FIG. 5c, the cathode of the LED 560 and the anode of the LED 562 are connected to a node A, and the cathode of the LED 562 and the anode of the LED 560 are connected to a node B. When an AC voltage is applied across the nodes A and B, the LEDs 560, 562 are energized on alternating halves of the AC waveform. In one embodiment, the plurality of LEDs 560, 562 can be implemented as a plurality of blue/UV LED chips, which can constitute the core of one or more white LEDs. In a further alternative embodiment, one or more additional LEDs can be connected in parallel with the LED 560, and, likewise, one or more additional LEDs can be connected in parallel with the LED 562, while maintaining the anti-parallel circuit configuration of the plurality of LEDs.

Figure 6:
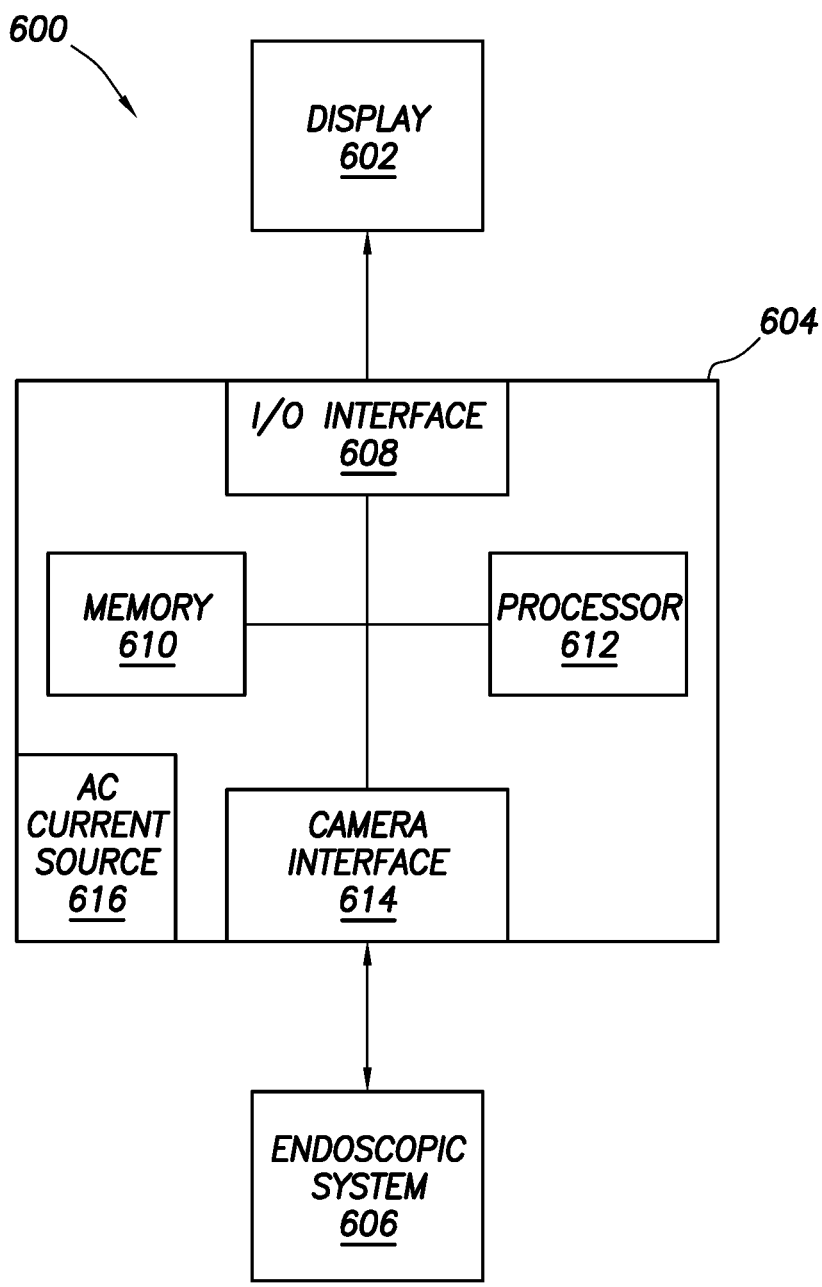
FIG. 6 is a block diagram of a computerized medical system incorporating the endoscopic system of FIG. 1.

FIG. 6 depicts an illustrative embodiment of an exemplary computerized medical system 600 that incorporates an endoscopic system 606, which can be like any one of the endoscopic systems 100, 300, 400, 500 described herein. As shown in FIG. 6, the computerized medical system 600 includes the endoscopic system 606, a computing device 604, and a display device 602. The endoscopic system 606 can send image data of a patient's internal anatomical structures to the computing device 604, which can receive the image data via, e.g., a suitable video/frame capture device. The computing device 604 can perform processing on the image data to segment target tissue and/or anatomical structures in the image data from other tissue and/or structures, and to display corresponding images on the display device 602 in a manner that conveys such segmentation to a user, such as a surgeon or other medical professional. The computing device 604 includes a camera interface 614 that can receive the image data from the endoscopic system 606, provide power (in conjunction with the AC current source 616) to the endoscopic system 606, and further provide bidirectional communications with the endoscopic system 606.

With regard to FIG. 6, the computing device 604 may be embodied as any suitable type of computing device, such as a personal computer, a workstation, a portable computing device, a console, a laptop, a tablet, a network terminal, an embedded device, or the like. The computing device 604 further includes an interconnection mechanism such as a data bus or other circuitry that couples the camera interface 614 to a memory 610, a processor 612, and an input/output (I/O) interface 608. The memory 610 may be embodied as any suitable type of computer readable medium, which may include, e.g., a floppy disk, a hard disk, a Read Only Memory (ROM), and/or a Random Access Memory (RAM). The memory 610 can store one or more software programs/applications for execution by the processor 612. The stored software program/applications may include instructions that, when executed by the processor 612, causes the processor 612 to perform various operations described herein. During operation of the computing device 604, the processor 612 can access the memory 610 via the interconnection mechanism in order to execute the software program/application(s). In other implementations, the processor 612 and the memory 610 may be replaced with programmable circuitry such as a field programmable gate array (FPGA), which may be programmed to execute the logic of the software program/application.

Figure 7:
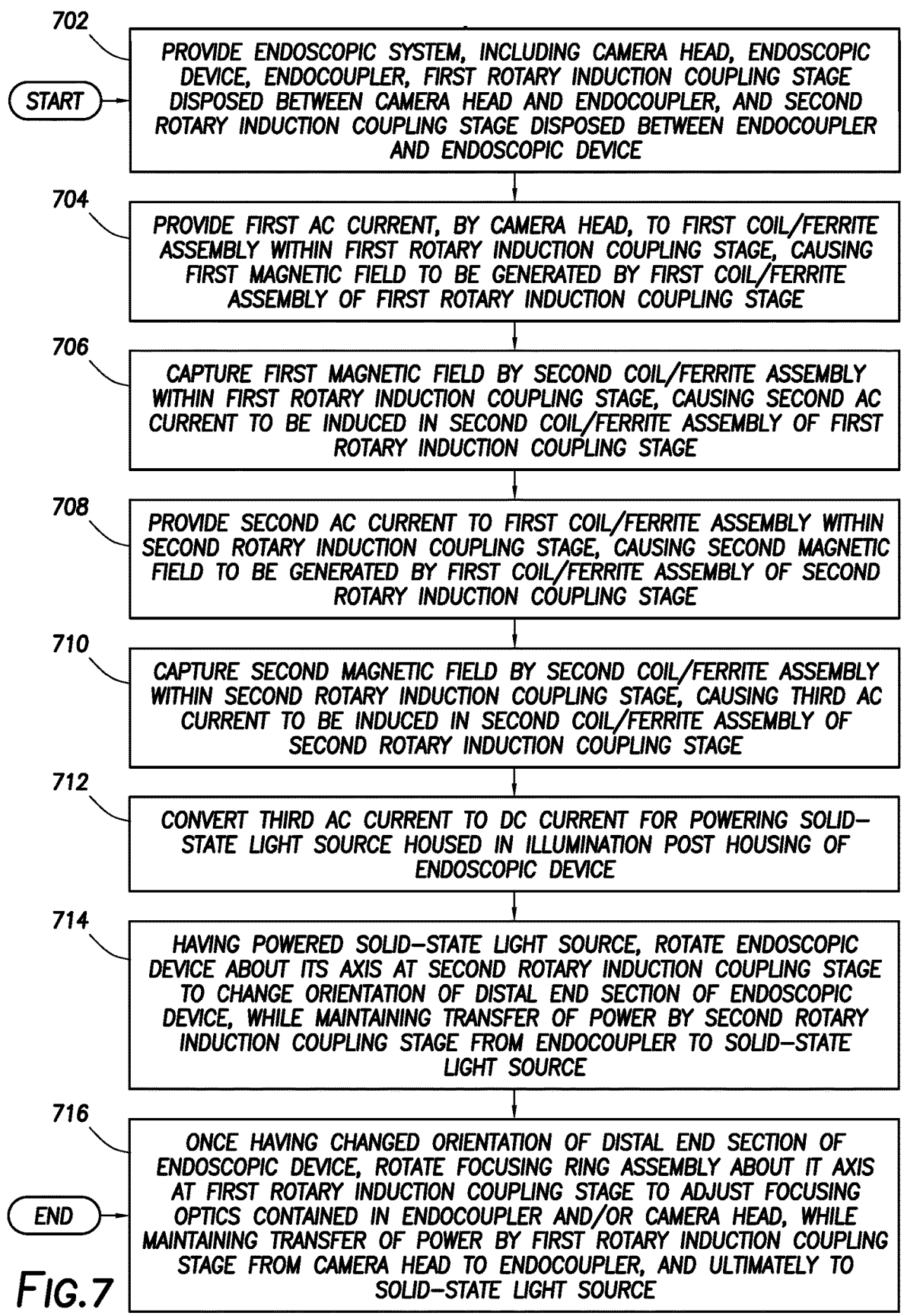
FIG. 7 is a flow diagram of an exemplary method of operating the endoscopic system of FIG. 1.

An exemplary method of operating the endoscopic system 100 is described below with reference to FIGS. 1, 2, and 7. As depicted in block 702 (see FIG. 7), the endoscopic system 100 (see FIG. 1) is provided, including the camera head 106, the endoscopic device 102, the endocoupler 104 coupling the camera head 106 to the endoscopic device 102, the first rotary induction coupling stage 202 (see FIG. 2) disposed between the camera head 106 and the endocoupler 104, and the second rotary induction coupling stage 204 (see also FIG. 2) disposed between the endocoupler 104 and the endoscopic device 102. As depicted in block 704, a first AC current is provided, by the camera head 106, to the first coil/ferrite assembly within the first rotary induction coupling stage 202, causing a first magnetic field to be generated by the first coil/ferrite assembly of the first rotary induction coupling stage 202. As depicted in block 706, the first magnetic field is captured by the second coil/ferrite assembly within the first rotary induction coupling stage 202, causing a second AC current to be induced in the second coil/ferrite assembly of the first rotary induction coupling stage 202. As depicted in block 708, the second AC current is provided to the first coil/ferrite assembly within the second rotary induction coupling stage 204, causing a second magnetic field to be generated by the first coil/ferrite assembly of the second rotary induction coupling stage 204. As depicted in block 710, the second magnetic field is captured by the second coil/ferrite assembly within the second rotary induction coupling stage 204, causing a third AC current to be induced in the second coil/ferrite assembly of the second rotary induction coupling stage 204. As depicted in block 712, the third AC current is converted to a DC current, which is provided for powering the solid-state light source housed in the illumination post housing 112 of the endoscopic device 102. As depicted in block 714, having powered the solid-state light source, the endoscopic device 102 is rotated, by a user (e.g., a surgeon or other medical professional), about its axis at the second rotary induction coupling stage 204 in order to change the orientation of the distal end section 120 of the endoscopic device 102, while maintaining the transfer of power by the second rotary induction coupling stage 204 from the endocoupler 104 to the solid-state light source housed in the endoscopic device 102. As depicted in block 716, once having changed the orientation of the distal end section 120 of the endoscopic device 102, a focusing ring assembly 114 implemented in the endocoupler 104 is rotated, by the user, about its axis at the first rotary induction coupling stage 202 in order to adjust focusing optics contained in the endocoupler 104 and/or the camera head 106, while further maintaining the transfer of power by the first rotary induction coupling stage 202 from the camera head 106 to the endocoupler 104, and ultimately to the solid-state light source housed in the endoscopic device 102.

It will be appreciated by those of ordinary skill in the art that modifications to and variations of the above-described systems and methods may be made without departing from the inventive concepts disclosed herein. Accordingly, the invention should not be viewed as limited except as by the scope and spirit of the appended claims.

The invention claimed is:

1. A method of operating an endoscopic system, comprising:
    applying, by a camera head having an image sensor, a first alternating current (AC current) to a first coil assembly of a first rotary induction coupling stage, wherein applying the first AC current creates a first magnetic field;
    capturing the first magnetic field by a second coil assembly of the first rotary induction coupling stage, wherein the capturing creates a second AC current induced in the second coil assembly;
    coupling the second AC current to a third coil assembly of a second rotary induction coupling stage, wherein applying the second AC current creates a second magnetic field;
    capturing the second magnetic field by a fourth coil assembly of the second rotary induction coupling stage, wherein capturing the second magnetic field creates a third AC current in the fourth coil assembly; and
    applying the third AC current to a solid-state light source contained in an endoscopic device.

2. The method of claim 1 further comprising, while coupling the third AC current to the solid-state light source, rotating the endoscopic device at the second rotary induction coupling stage about an axis of the endoscopic system to change an orientation of a distal end of the endoscopic device relative to the camera head.

3. The method of claim 2 further comprising, after rotating the endoscopic device at the second rotary induction coupling, turning a focusing ring assembly implemented in an endocoupler disposed between the camera head and the endoscopic device while maintaining a rotational relationship of the distal end of the endoscopic device and the camera head about the axis of the endoscopic system, the second coil assembly of the first rotary induction coupling stage and the third coil assembly of the second rotary induction coupling stage disposed within the endocoupler.

4. The method of claim 1 wherein applying the first AC current further comprises applying the first AC current to the first coil assembly disposed within the camera head.

5. The method of claim 1 wherein capturing the second magnetic field further comprises capturing the second magnetic field by the fourth coil assembly disposed in the endoscopic device.

6. The method of claim 1 further comprising:
    turning a focusing ring assembly of an endocoupler, the focusing ring assembly disposed between the camera head and the endoscopic device; and
    simultaneously maintaining a rotational relationship of a distal end of the endoscopic device and the camera head about the an axis of the endoscopic system.

7. The method of claim 6 wherein turning the focusing ring assembly while maintaining the rotational relationship of the distal end of the endoscopic device and the camera head further comprises conducting the second AC current along a conductor within the endocoupler to the third coil assembly.

8. The method of claim 6 wherein turning the focusing ring assembly while maintaining the rotational relationship of the distal end of the endoscopic device and the camera head further comprises:
    applying the second AC current to a fifth coil assembly of a third rotary induction coupling stage of the endocoupler, wherein applying the second AC current creates a third magnetic field;
    capturing the third magnetic field by a sixth coil assembly of the third rotary induction coupling stage of the endocoupler, wherein capturing the third magnetic field creates a fourth AC current in the sixth coil assembly; and
    applying the fourth AC current to the third coil assembly.

* * * * *